United States Patent [19]

Shanklin, Jr. et al.

[11] Patent Number: 4,812,452
[45] Date of Patent: Mar. 14, 1989

[54] 1-((AMINOALKYL AND AMINOALKYLAMINO) CARBONYL AND THIOCARBONYL)-α,α-DIARYLPYRROLIDINE, PIPERIDINE AND HOMOPIPERIDINEACETAMIDES AND ACETONITRILES

[75] Inventors: James R. Shanklin, Jr.; James M. Wilkinson, II, both of Richmond, Va.

[73] Assignee: A. H. Robins Company, Incorporated, Richmond, Va.

[21] Appl. No.: 845,170

[22] Filed: Mar. 27, 1986

Related U.S. Application Data

[62] Division of Ser. No. 662,583, Oct. 19, 1984, Pat. No. 4,594,343.

[51] Int. Cl.$^4$ .................. A61K 31/445; C07D 211/34
[52] U.S. Cl. ........................................ 514/212; 540/597;
540/598; 540/602; 540/607; 544/130; 544/141;
544/360; 546/188; 546/189; 546/208; 546/226;
548/523; 548/524; 548/538; 548/540;
514/235.5; 514/237.2; 514/252; 514/316;
514/326; 514/330; 514/422; 514/423
[58] Field of Search .............. 546/208, 188, 189, 226;
514/330, 408, 423, 428, 212, 235.5, 237.2, 252,
316, 326, 422; 548/518, 523, 524, 538, 540;
540/602, 607, 597, 598; 544/130, 141, 360

[56] References Cited

U.S. PATENT DOCUMENTS

| | | | |
|---|---|---|---|
| 2,957,881 | 10/1960 | Hoffmann et al. | 546/189 |
| 3,527,762 | 9/1970 | Jack et al. | 546/189 |
| 3,639,476 | 1/1972 | Eberle et al. | 548/540 |
| 3,956,296 | 5/1976 | Duncan, Jr. et al. | 546/208 |
| 4,002,766 | 1/1977 | Welstead, Jr. | 514/408 |
| 4,098,890 | 7/1978 | Molloy | 514/408 |
| 4,163,790 | 8/1979 | Franko et al. | 514/330 |
| 4,318,913 | 3/1982 | Clitherow et al. | 514/212 |
| 4,547,514 | 10/1985 | Mathur et al. | 514/327 |

Primary Examiner—Richard L. Raymond
Assistant Examiner—P. Weaster

[57] ABSTRACT

Novel 1-[(aminoalkyl and aminoalkylamino)carbonyl and thiocarbonyl]-α,α-diaryl-pyrrolidine, piperidine and homopiperidineacetamides and acetonitriles having the formula:

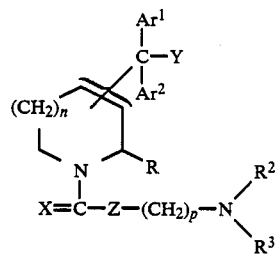

wherein;
n is zero, one or two;
X is oxygen or sulfur;
Z is

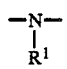

or —(CH$_2$);
p is 0 to 5 inclusive with the proviso that when Z is

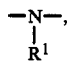

p is at least one;
Y is aminocarbonyl or cyano;
Ar$^1$ and Ar$^2$ are 2, 3 or 4-pyrido, phenyl or substituted phenyl;
R is hydrogen or loweralkyl;
R$^1$, R$^2$ and R$^3$ are hydrogen, cycloalkyl, loweralkyl, phenyl, substituted phenyl, phenylloweralkyl, and R$^2$ and R$^3$ taken with the adjacent nitrogen may form a heterocyclic residue, and diastereoisomers when possible and pharmaceutical salts; and the method and pharmaceutical compositions for treating cardiac arrhythmias therewith are disclosed.

9 Claims, No Drawings

1-((AMINOALKYL AND AMINOALKYLAMINO) CARBONYL AND THIOCARBONYL)-α,α-DIARYLPYRROLIDINE, PIPERIDINE AND HOMOPIPERIDINEACETAMIDES AND ACETONITRILES

This is a division of application Ser. No. 662,583, filed Oct. 19, 1984, now U.S. Pat. No. 4,594,343.

BACKGROUND OF THE INVENTION

1. Field of the Invention

The present invention relates to novel 1-[(aminoalkyl and aminoalkylamino)carbonyl and thiocarbonyl]-α,α-diphenyl-3-pyrrolidineacetamides and acetonitriles and corresponding 3 and 4-piperidine and homopiperidineacetamides and acetonitriles and a process for administering the same to a living animal body for the cardiac antiarrhythmic effect and pharmaceutical methods and compositions associated therewith.

2. Information Disclosure Statement

3-Pyrrolidinyl-α,α-diphenylacetamides, acetonitriles and methanes having antiarrhythmic activity are disclosed in U.S. Pat. No. 4,002,766 and have the general formula:

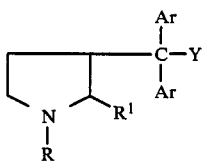

wherein R is selected from hydrogen, loweralkyl, lowercycloalkyl or phenylloweralkyl; $R^1$ is hydrogen or loweralkyl; Ar is phenyl and among the radicals disclosed for Y are carbamoyl and cyano. In contrast, while the pyrrolidine compounds in the present invention have similarly positioned carbamoyl or cyano radicals, the substituents at the one position are entirely different, having at least a carbonyl or thiocarbonyl interposed and a terminal amino group.

OBJECTS AND SUMMARY OF THE INVENTION

The novel compounds of this invention have the formula:

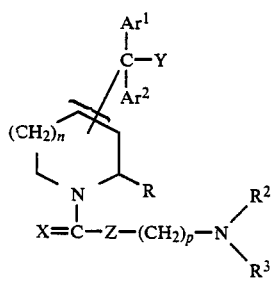

Formula I wherein;
n is selected from zero, one or two;
X is selected from oxygen or sulfur;
Z is selected from

or —CH$_2$—;

p is selected from 0 to 5 inclusive with the proviso that when Z is

p is at least one;

Y is selected from aminocarbonyl or cyano;
$Ar^1$ and $Ar^2$, which may be the same or different, are selected from the group consisting of 2, 3 or 4-pyrido, phenyl or phenyl substituted by 1 to 3 radicals which may be the same or different selected from loweralkyl, loweralkoxy, halogen or trifluoromethyl;
R is selected from hydrogen or loweralkyl;
$R^1$, $R^2$ and $R^3$ are selected from the group consisting of hydrogen, cycloalkyl, loweralkyl, phenyl, phenyl substituted by halogen, loweralkyl, or loweralkoxy and phenyl-loweralkyl wherein phenyl may be substituted by halogen, loweralkyl or loweralkoxy and $R^1$, $R^2$ and $R^3$ may be the same or different, and $R^2$ and $R^3$ taken together with the adjacent nitrogen atom may form a heterocyclic residue selected from pyrrolidino, piperidino, 4-phenylpiperidino, 2,6-diloweralkyl-piperidino, 4hydroxy-4-phenylpiperidino, 4-cyano-4-phenylpiperidino, 4-phenyl-1,2,3,6-tetrahydropiperidino, piperazino, 4-loweralkylpiperazino, 4-phenylpiperazino, (4-phenylloweralkyl)-piperazino, or 4-morpholino radicals;
and when the side group

is in the 3-position and $Ar^1$ and $Ar^2$ are dissimilar, the diastereoisomers thereof; and the pharmaceutically acceptable acid addition salts thereof.

The 1-[(aminoalkyl)carbonyl and thiocarbonyl]-α,α-diarylpyrrolidine, piperidine and homopiperidineacetamides and acetonitriles encompassed by Formula I wherein Z is —CH$_2$—, have the formula:

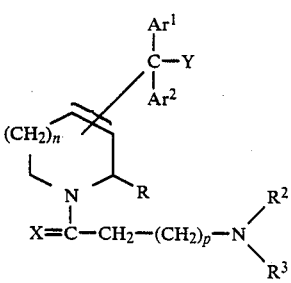

Formula Ia wherein n, $Ar^1$, $Ar^2$, Y, X, R, $R^2$ and $R^3$ are as defined under Formula I and p is selected from zero to 5 inclusive and the salts and isomers of Formula I.

The 1-[(aminoalkylamino)carbonyl and thiocarbonyl]-α,α-diarylpyrrolidine, piperidine and homopiperidine acetamides and nitriles encompassed by Formula I wherein Z is

have the formula:

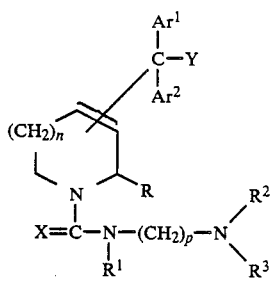

Formula Ib wherein $Ar^1$, $Ar^2$, Y, X, R, $R^1$, $R^2$ and $R^3$ are as defined under Formula I and p is selected from 1 to 5 inclusive and the salts and isomers of Formula I.

In the further definition of symbols in the formulas hereof and where they appear elsewhere throughout this specification and claims, the terms have the following significance.

The term "loweralkyl" as used herein includes straight and branched chain radicals of up to eight carbons inclusive and is exemplified by such groups as methyl, ethyl, propyl, isopropyl, butyl, sec-butyl, tertbutyl, amyl, isoamyl, hexyl, heptyl and octyl radicals and the like. The term "loweralkoxy" has the formula "—O—loweralkyl."

The term "cycloalkyl" as used herein includes primarily cyclic alkyl radicals containing 3 to 9 carbon atoms inclusive and includes such groups as cyclopropyl, cyclobutyl, cyclopentyl, cyclohexyl, methylcyclohexyl, cycloheptyl and the like.

The term "halogen" when referred to herein includes fluorine, chlorine, bromine and iodine, preferably fluorine, chlorine and bromine.

"Pharmaceutically acceptable acid addition salts" are those salts formed by the compounds with any acid which is physiologically compatible in warm-blooded animals, such salts being formed by either strong or weak acids. Representative of strong acids are hydrochloric, hydrobromic, sulfuric and phosphoric acids. Representative of weak acids are fumaric, maleic, succinic, tartaric, oxalic, citric, hexamic and the like.

The compounds of the present invention exhibit cardiac antiarrhythmic activity in dogs in the Ouabain and Ligation arrhythmia models as explained more fully hereinbelow under "Pharmacology."

The method of treating cardiac arrhythmias in living animals comprises administering the compounds of Formula I to a living animal body for cardiac antiarrhythmia effect in an effective amount to control arrhythmia as set forth hereinbelow under "Pharmaceutical Compositions and Administration." The compounds of Formula I wherein Y is an acetamido radical are preferred for their antiarrhythmic effect.

It is therefore an object of the present invention to provide certain novel 1-[(aminoalkyl)carbonyl and thiocarbonyl]-α,α-diarylpyrrolidine, piperidine and homopiperidineacetamides and acetonitriles, methods of preparing the same and methods and compositions for treating cardiac arrhythmias in living animals therewith.

Another object is to provide certain novel 1-[(aminoalkylamino)carbonyl and thiocarbonyl]-α,α-diarylpyrrolidine, piperidine and homopiperidineacetamides and acetonitriles, methods of preparing the same and methods and compositions for treating cardiac arrhythmias in living animals therewith.

Additional objects will be apparent to one skilled in the art and still other objects will become apparent hereinafter.

DETAILED DESCRIPTION OF THE INVENTION

The novel compounds as composition of matter set forth in Formula I above are utilized in pharmaceutical compositions in the novel method of treating living animals in an amount effective for controlling cardiac arrhythmias.

The 1-[(aminoalkyl)carbonyl and thiocarbonyl] derivatives of Formula Ia encompassed by Formula I are prepared by Method A which is represented by the following equation:

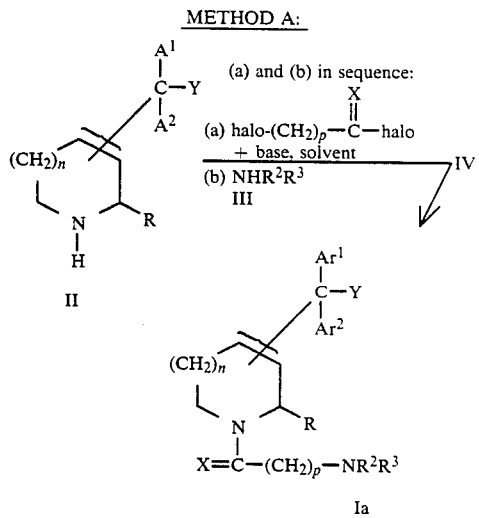

X = O or S wherein $Ar^1$, $Ar^2$, Y, X, p, n, R, $R^2$ and $R^3$ are selected from the values assigned under Formula I.

Generally, in Method A a 1-unsubstituted heterocyclicamine acetamide or acetonitrile (II) are reacted with a dihalo compound:

in the presence of base such as sodium or potassium carbonate in a suitable solvent. The product mix is then reacted with an amine

at room temperature for several hours and then concentrated. The residue is then partitioned between dilute aqueous base and a suitable solvent such as methylene chloride. The solvent layer is dried and concentrated to give the free base of compounds of Formula Ia which may be converted to acid addition salts in a suitable solvent. The salts may be recrystallized from mixtures of suitable solvents.

The 1-(aminoalkylamino)carbonyl derivatives of Formula Ib encompassed by Formula I are prepared by Methods B and C.

Method B is represented by the following equation:

METHOD B:

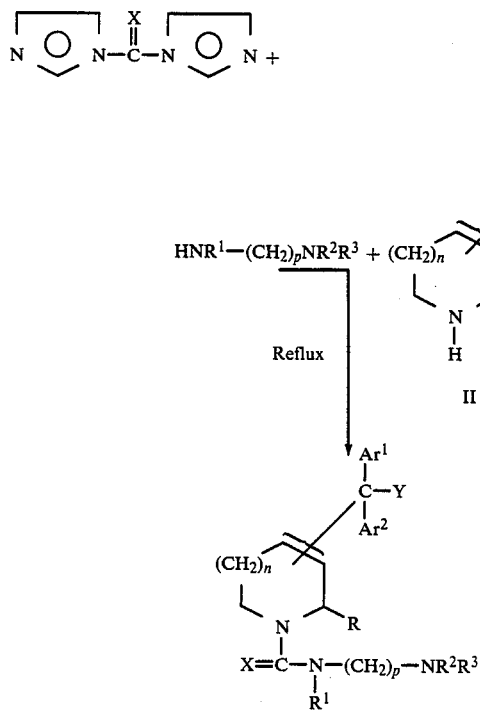

(Solvent, RT)

wherein $Ar^1$, $Ar^2$, Y, X, p, n, R, $R^1$, $R^2$ and $R^3$ are selected from the values assigned under Formula I with the proviso that $R^2$, $R^3$=alkyl or aryl and $R^1$=H.

Generally, in Method B an alkyldiamine, V, is reacted first with 1,1-carbonyldiimidazole (or 1,1-thiocarbonyldiimidazole) in a suitable solvent (e.g., tetrahydrofuran) at room temperature followed by reaction at gentle reflux with the 1-unsubstituted-heterocyclicamine acetamide or acetonitrile (II). Usually, reaction is effected by refluxing for several hours after which the mixture is cooled and concentrated. The residue is taken up in a solvent such as methylene chloride and washed to remove impurities and the product obtained by evaporating the methylene chloride to obtain the free base of compounds of Formula Ib and, if desired, converting to an acid addition salt in a suitable solvent and recrystallizing from a suitable solvent mixture. The method is illustrated in Example 6.

Method C is represented by the following equation:

METHOD C:

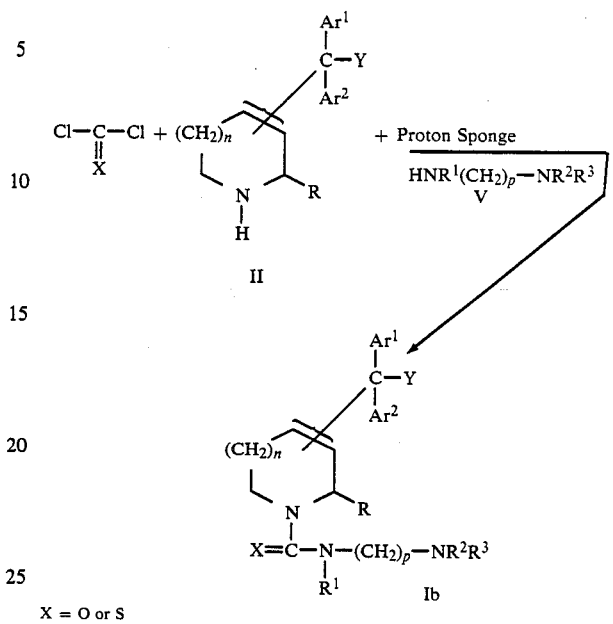

X = O or S wherein $Ar^1$, $Ar^2$, Y, X, p, R, $R^1$, $R^2$ and $R^3$ are selected from values assigned under Formula I with the proviso that when $R^1$ is not hydrogen, $R^2$ and $R^3$ must be other than hydrogen, or $R^1$ is the same as $R^2$, and $R^3$ is hydrogen.

Generally, in Method C the 1-unsubstituted heterocyclic compound is reacted with phosgene (or thiophosgene) in a suitable organic solvent plus Proton Sponge®, which is 1,8-bis-(dimethylamino)naphthylene followed by extraction (washing) with dilute sulfuric acid, and the organic layer is dried and evaporated to an oil. The oil is dissolved in tetrahydrofuran and reacted with an amine of Formula V. The reaction mixture is stripped to dryness and the residue is partitioned between water and a suitable organic solvent. Evaporation of the solvent yields the crude free base, Ib.

As can be seen in the foregoing process description and following examples, compounds of Formula I are either isolated as the free base by evaporating or crystallizing or as an acid addition salt by reaction with the desired acid using conventional means, crystallizing and recrystallizing from a suitable solvent or mixture of solvents, usually an alcohol and an ester or ether.

Salts of compounds of Formula I, Ia and Ib may be converted to the free base by partitioning between a solvent such as methylene chloride and an aqueous base such as sodium hydroxide and evaporating the solvent layer in vacuo.

As mentioned above, the prior art discloses methods of preparing 1-unsubstituted hydroxyhomopiperidines which are used to prepare the homopiperidine derivatives of this invention.

A general method for the preparation of 1-unsubstituted-3 and 4-[α,α-diarylacetonitrilo and acetamido]-pyrrolidines, piperidines and homopiperidines is outlined by schematic equation in Chart I.

CHART I

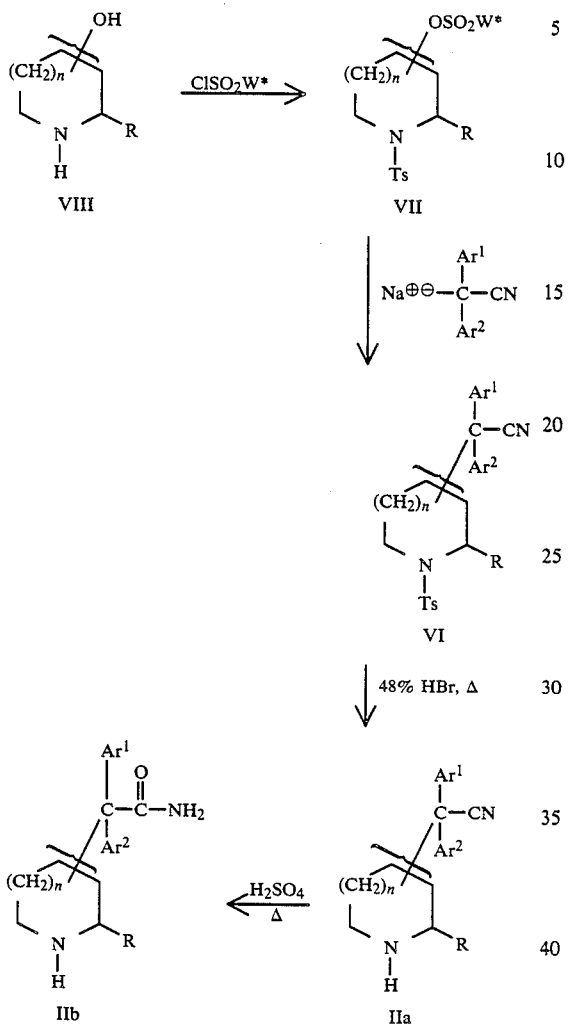

*W = alkyl, phenyl or substituted phenyl.

Another method for the preparation of 1-unsubstituted 3-[α,α-diarylacetonitrilo and acetamido]pyrrolidines and 1-unsubstituted 4-[α,α-diarylacetonitrilo and acetamido]piperidines and homopiperidines is outlined in Chart II.

CHART II

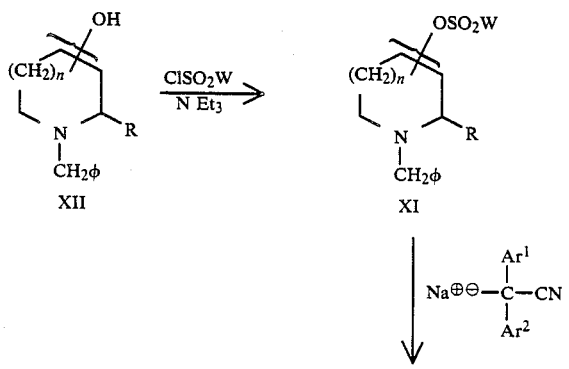

W = loweralkyl or tosyl

The following preparations serve to illustrate the synthesis of certain precursors required in making the compounds of Formula I but are not limiting as to scope. The preparation of certain 1-unsubstituted-α,α-diarylacetonitrilo and acetamido-pyrrolidinyl precursors is taught in U.S. Pat. No. 4,002,766.

PREPARATION 1

α,α-Diphenyl-1-(phenylmethyl)-3-pyrrolidineacetonitrile

The title compound was prepared from 1-(phenylmethyl)-3-pyrrolidinol, methanesulfonylchloride, triethylamine and sodium diphenylacetonitrile by the procedure of U.S. Pat. No. 3,192,210, b.p. 215–218/0.01 mm.

PREPARATION 2

1-[(4-Methylphenyl)sulfonyl]-3-piperidino-4-methylphenylsulfonate ester

A solution of 73.5 g (0.728 mole) of 3-hydroxy piperidine and 350 g (1.84 mole) of p-toluenesulfonyl chloride in 1 liter of pyridine was stirred at room temperature for 17.5 hr. The solution was quenched in 1 liter of water.

The aqueous mixture was extracted with several portions of methylene chloride and the combined methylene chloride layers were extracted with several portions of 1M sulfuric acid and then with several portions of 1M sodium hydroxide. The organic solution was dried over magnesium sulfate and the solvent was removed in vacuo to give an oil residue. Crystalline product was obtained from the oil residue using the solvent pair, diethyl ether methylene chloride, m.p. 132°–133° C.

Analysis: Calculated for $C_{19}H_{23}NO_5S_2$: C, 55.73; H, 5.66; N, 3.42. Found: C, 55.79; H, 5.69; N, 3.38.

PREPARATION 3

3-(Cyanodiphenylmethyl)-1-pyrrolidinecarboxylic acid, methyl ester

To a solution of 36.5 g (0.10 mole) of α-(1-benzyl-3-pyrrolidinyl)-α,α-diphenylacetonitrile and 8.7 g (0.11 mole) of pyridine in methylene chloride was added dropwise at 25° C., 10.4 g (0.11 mole) of methyl chloroformate. The solution was refluxed for 16 hr. To the refluxing solution was added 26.1 g (0.33 mole) of pyridine and 31.2 g (0.33 mole) additional methyl chloroformate. Heating at reflux was continued for 5 hr. The mixture was cooled and washed four times with water. The methylene chloride layer was dried and concentrated in vacuo. The residual oil was crystallized twice from a mix of petroleum ether (30°–60°) and isopropanol to give 20 g (68%) of title product, m.p. 133°–135° C.

Analysis: Calculated for $C_{20}H_{20}N_2O_2$: C, 74.98; H, 6.29; N, 8.74. Found: C, 75.03; H, 6.44; N, 8.66.

PREPARATION 4

α,α-Diphenyl-3-pyrrolidineacetamido oxalate

A stirred solution of 22.0 g (0.060 mole) of α,α-diphenyl-3-pyrrolidineacetonitrile in 100 ml of conc. sulfuric acid was heated at 70° C. for 24 hr and then cooled. The cold reaction mixture was poured over ice and basified with 50% sodium hydroxide and ice. The mixture was extracted with chloroform. The chloroform extract was washed with water, dried over sodium sulfate and concentrated in vacuo to give the free base of the title compound. The free base was reacted with oxalic acid and crystallized from isopropyl alcohol to give 15 g of title product, m.p. 216°–218.5° C.

PREPARATION 5

3-(Cyanodiphenylmethyl)-1-pyrrolidinecarboxylic acid, phenyl ester

To a solution of 47 g (0.13 mole) of α-(1-benzyl-3-pyrrolidinyl)-α,α-diphenylacetonitrile and 10.58 g (0.13 mole) of pyridine in 400 ml of methylene chloride was added, dropwise at 0° C., 62.7 g (0.39 mole) of phenyl chloroformate. The reaction mixture was refluxed for 16 hr. The mixture was cooled and washed 3 times with water and twice with dilute sodium hydroxide solution. The methylene chloride layer was then dried, filtered and concentrated in vacuo. The resulting solid was recrystallized twice from ethyl acetate to give 23 g (50%) of title compound, m.p. 154°–155° C.

Analysis: Calculated for $C_{25}H_{22}N_2O_2$: C, 78.51; H, 7.32; N, 5.79. Found: C, 78.31; H, 7.43; N, 5.74.

PREPARATION 6

α,α-Diphenyl-3-pyrrolidineacetamide

A solution of 3.0 g (0.008 mole) of 3-(cyanodiphenylmethyl)-1-pyrrolidinecarboxylic acid phenyl ester in 100 ml of 90% sulfuric acid was stirred at 70° C. for 20 hr. The reaction mixture was cooled, poured over ice and basified by adding, alternately, 50% sodium hydroxide and ice. The mixture was extracted with chloroform. The chloroform extract was washed with water, dried over sodium sulfate and concentrated in vacuo. The residue was crystallized in ethyl acetate. Recrystallization from ethyl acetate-ethanol gave 1.4 g (65%) of title product, molecular ion at 281 by mass spectrometer analysis.

PREPARATION 7

α,α-Diphenyl-3-pyrrolidineacetonitrile oxalate [1:1]

Preparation of Lithium n-propyl-Mercaptide Reagent

To a mixture of 8.9 g (1.12 mole) of lithium hydride in 350 ml of hexamethylphosphoramide under a nitrogen atmosphere was added, dropwise at 10° C., 78.65 g (1.03 mole) of n-propanethiol. Stirring was continued for 3 hr and the mixture was filtered under nitrogen atmosphere. The reagent was titrated with 0.1N hydrochloric acid to a phenolphthalein end point. The normality of the reagent was 0.74N.

To 320 ml (0.24 mole) of the foregoing lithium n-propyl mercaptide reagent was added, portionwise at 25° C., 14 g (0.044 mole) of 3-(cyanodiphenylmethyl)-1-pyrrolidinecarboxylic acid, methyl ester. Stirring was continued at 25° C. for 16 hr and then at 50°–60° C. for 2 hr. The mixture acidified with 6N hydrochloric acid and then stirred at 60°–70° C. for 20 min. The mixture was cooled and extracted 3 times with isopropyl ether. The aqueous layer was separated, basified with dilute sodium hydroxide and extracted 3 times with isopropyl ether. These last ether extracts were washed 3 times with water, dried and concentrated in vacuo. The residue was reacted with oxalic acid crystallizing the oxalate salt from isopropanol-water to give a 64% yield of the title compound. A portion was recrystallized from isopropanol-water, m.p. 181°–184° C. (with decomposition).

Analysis: Calculated for $C_{20}H_{20}N_2O_4$: C, 68.17; H, 5.72; N, 7.95. Found: C, 68.05; H, 5.68; N, 7.93.

PREPARATION 8

α,α-Diphenyl-1-phenylmethyl-3-pyrrolidineacetamide

To 250 ml of concentrated sulfuric acid under agitation was added, slowly at 70° C., 170 g (0.48 mole) of α-(1-benzyl-3-pyrrolidinyl)-α,α-diphenylacetonitrile. Stirring was continued for 16 hr at 75°–80° C. The solution was cooled and poured into a mixture of ice, 50% sodium hydroxide solution and chloroform. The chloroform layer was separated and the aqueous phase extracted three more times with chloroform. The combined chloroform layers were dried and concentrated in vacuo to give 188 g of residual oil. A portion of the oil was crystallized in isopropanol and the solid recrystallized from a mix of isopropanol and isopropyl ether to give a light brown solid, m.p. 135°–138° C.

Analysis: Calculated for $C_{25}H_{26}N_2O$: C, 81.05; H, 7.07; N, 7.56. Found: C, 80.95; H, 7.21; N, 7.59.

PREPARATION 9

α,α-Diphenyl-3-pyrrolidineacetamide maleate [1:1]

A solution of 1.13 g of 1-benzyl-α,α-diphenyl-3-pyrrolidineacetamide in 50 ml of methanol was subjected to catalytic hydrogenation (over 0.5 g of 10% palladium-on-charcoal catalyst) at 75° C. overnight in a Parr hydrogenation apparatus. The mixture was filtered and the filtrate was concentrated to give 0.783 g (80%) free base of the title compound as light tan gum. The mass spectra and infrared spectra were consistent with the structure. To a methanol solution of a portion of the free base was added a methanolic solution of maleic acid. The solution was concentrated to remove methanol and the residue crystallized. The solid was recrystallized twice from isopropanol-diethyl ether. The solid was dried at 110°/0.1 mm for 3 hr. The product liquefied over a range of 110°–145° C.

Analysis: Calculated for $C_{22}H_{24}N_2O_5$: C, 66.65; H, 6.10; N, 7.07. Found: C, 66.79; H, 6.05; N, 7.04.

PREPARATION 10

α,α-Diphenyl-3-pyrrolidineacetamide N-cyclohexylsulfamate hydrate [3:2]

A methanolic solution of 1.15 g of α,α-diphenyl-3-pyrrolidineacetamide and 0.735 g of hexamic acid was prepared and the methanol was evaporated from the solution to give a crystalline residue. The residue was recrystallized from ethanol, m.p. 103°–106° C.

Analysis: Calculated for $C_{48}H_{72}N_6O_{11}$: C, 59.24; H, 7.46; N, 8.64. Found: C, 58.97; H, 6.98; N, 8.51.

PREPARATION 11

α,α-Diphenyl-1-(phenylmethyl)-4-piperidineacetonitrile hydrochloride

To a prewashed slurry of 8.0 g (0.19 mole) of 57% sodium hydride in 300 ml of dimethylsulfoxide was added 32.8 g (0.17 mole) of diphenylacetonitrile. The solution was heated at 65° C. for 1 hr, during which time the solution developed a deep red color. To the reaction mixture was added 55.90 g (0.16 mole) of 1-(phenylmethyl)-4-piperidinol ester with 4-methylbenzenesulfonic acid in 50 ml of dimethylsulfoxide and the solution was stirred overnight at 60° C. The solution was cooled and poured into 1 liter of water. The aqueous solution was extracted three times with 150 ml portions of toluene. The toluene extracts were combined and 500 ml of 1N sulfuric acid was added. A gummy residue precipitated which was separated and partitioned with methylene chloride and 10% aqueous sodium hydroxide. The aqueous layer was extracted with methylene chloride and the combined methylene chloride extracts were dried over magnesium sulfate and concentrated to give 35.0 g (57%) of free base of the title compound as tan solid, m.p. 138°–142° C. A portion of the free base in methanol was reacted with ethereal hydrogen chloride to give the hydrochloride salt, m.p. >250° C.

Analysis: Calculated for $C_{26}H_{27}ClN_2$: C, 77.50; H, 6.75; N, 6.95. Found: C, 77.09; H, 6.76; N, 7.04.

PREPARATION 12

α,α-Diphenyl-1-[4-(methylphenyl)sulfonyl]-3-piperidineacetonitrile

To a slurry of 0.15 g (0.012 mole) of prewashed sodium hydride in 100 ml of toluene was added 2.10 g (0.011 mole) of diphenylacetonitrile. The solution was refluxed for 2 hrs and 4.0 g (0.010 mole) of 1-[(4-methylphenyl)sulfonyl]-3-piperidinol-(4-methylphenyl)sulfonate ester in 100 ml of toluene was added. The solution was refluxed for 18 hr, cooled, washed three times with 100 ml portions of water and dried over magnesium sulfate. The solution was evaporated to a gummy residue which was crystallized from absolute ethanol to give 2.50 g (58%) of a pale yellow powder, m.p. 135°–136° C.

Analysis: Calculated for $C_{19}H_{26}N_2O_2S$: C, 72.53; H, 6.09; N, 6.51. Found: C, 72.79; H, 6.10; N, 6.52.

PREPARATION 13

α,α-Diphenyl-3-piperidineacetonitrile hydrochloride

A solution of 5.00 g (0.012 mole) of α,α-diphenyl-1-[4-(methylphenyl)sulfonyl]-3-piperidineacetonitrile, 60 ml of 48% hydrobromic acid and about 5 g phenol (excess) was refluxed for 3.5 hr. The solution was cooled, poured onto ice and made basic with an excess of 50% sodium hydroxide. The mixture was extracted with three 150 ml portions of methylene chloride. The combined methylene chloride layers were dried and concentrated to give a black oily residue. The residue was taken up in 1:1 isooctane/toluene solution and the mixture was extracted with 10% aqueous hydrochloric acid solution. The acidic extract was made basic with 10% sodium hydroxide and extracted with methylene chloride. The extracts were dried over magnesium sulfate and concentrated to give 1.70 g (84%) of the free base of the title compound as a glassy residue. The free base was dissolved in isopropyl alcohol and reacted with ethereal hydrogen chloride to give the hydrochloride salt. The salt was recrystallized from ethanol/ethyl acetate to give 1.79 g (48%) of the title product, m.p. 171°–177° C.

Analysis: Calculated for $C_{19}H_{21}ClN_2$: C, 72.95; H, 6.77; N, 8.95. Found: C, 72.64; H, 6.73; N, 8.90.

PREPARATION 14

4-Cyanodiphenylmethyl)-1-piperidinecarboxylic acid phenyl ester

To a solution of 34.0 g (0.093 mole) of α,α-diphenyl-1-(phenylmethyl)-4-piperidineacetonitrile in 300 ml of methylene chloride was added dropwise to 15.70 g (0.10 mole) of phenylchloroformate in 100 ml of methylene chloride. The solution was stirred 3 hr at room temperature, after which 11.10 g (0.11 mole) of triethylamine was added. The solution was stirred additionally for 1 hr, washed with 200 ml of water followed by 100 ml of 10% hydrochloric acid and dried over magnesium sulfate. The methylene chloride layer was concentrated to give a tan colored paste. The paste was recrystallized from isopropyl alcohol to give 19.70 g (54%) of solid. A portion of the solid was recrystallized from isopropyl alcohol, m.p. 141°–143° C.

Analysis: Calculated for $C_{26}H_{24}N_2O_2$: C, 78.76; H, 6.10; N, 7.06. Found: C, 78.38; H, 6.27; N, 7.01.

PREPARATION 15

α,α-Diphenyl-4-piperidineacetamide fumarate monohydrate

A solution of 18.50 g (0.046 mole) of 4-(cyanodiphenylmethyl)-1-piperidinecarboxylic acid phenyl ester in 100 ml of 90% sulfuric acid was heated at 65° C. for 18 hr and 90° C. for 6 hr. The mixture was cooled, poured onto ice and made basic with excess 50% sodium hydroxide. The aqueous solution was extracted with three 150 ml portions of chloroform. The combined chloroform extract was dried over magnesium sulfate and concentrated to give a residue which crystallized on standing. Recrystallization of the residue from ethanol/ethyl acetate gave 6.10 g (45%) of the free base of the title compound. A 1 g portion was reacted with fumaric acid, crystallizing from methanol-diethyl ether to yield 1.0 g of the salt, m.p. 172°–175° C. (softens at 158° C.).

Analysis: Calculated for $C_{23}H_{26}N_2O_6$: C, 64.47; H, 6.59; N, 6.54. Found: C, 64.76; H, 6.13; N, 6.55.

PREPARATION 16

α,α-Diphenyl-3-piperidineacetamide hemifumarate hemihydrate

A solution of 2.3 g (0.0086 mole) of crude α,α-diphenyl-3-piperidineacetonitrile hydrochloride in 50 ml of 90% sulfuric acid was heated at 80° C. for 18 hr. The solution was cooled, made basic with excess 50% sodium hydroxide and extracted with methylene chloride. The extract was dried over magnesium sulfate and concentrated to yield 1.5 g (59%) of crude free base of the title compound. The fumarate was prepared in methanol using 0.5 equivalent of fumaric acid and adding diethyl ether to precipitate and give 0.50 g (16%) of title product, m.p. >250° C.

Analysis: Calculated for $C_{21}H_{25}N_2O_{3.5}$: C, 69.78; H, 6.97; N, 7.75. Found: C, 69.75; H, 6.90; N, 7.68.

PREPARATION 17

1-(Phenylmethyl)-4-piperidinol ester with 4-methylbenzenesulfonic acid maleate [1:1]

A solution of 100 g (0.524 mole) of N-benzyl-4-hydroxypiperidine and 13 g (0.684 mole) of tosylchloride in 600 ml of pyridine was stirred at room temperature overnight. One liter of methylene chloride and 500 ml of 0.5M aqueous sodium hydroxide were added to the reaction mixture. The reaction mixture was stirred for 10 min and the phases were separated. The methylene chloride layer was extracted with several portions of dilute sodium hydroxide, dried over magnesium sulfate and evaporated in vacuo to give an oil, the free base of the title compound. The free base was converted to the maleate salt which was recrystallized from methylene chloride-diethyl ether to give white crystalline solid, m.p. 159°–160° C.

Analysis: Calculated for $C_{23}H_{27}NO_7S$: C, 59.86; H, 5.90; N, 3.04. Found: C, 59.79; H, 5.86; N, 2.95.

PREPARATION 18

α-(4-Chlorophenyl)-α-[1-(phenylmethyl)-3-pyrrolidinyl]-2-pyridineacetonitrile α isomer

*Diastereoisomer designated α-isomer as first emerging from the HPLC column.

To a solution of 136 g (0.77 mole) of 1-benzyl-3-pyrrolidinol and 78 g (0.79 mole) of triethylamine in 600 ml of dry benzene was added dropwise 8.86 g (0.77 mole) of methanesulfonyl chloride while cooling with an ice bath. The ice bath was removed and the mixture stirred 1 hr. and filtered. The filter cake was washed twice with 100 ml of benzene.

In a separate flask, 175 g (0.77 mole of α-(4-phenyl)-2-pyridylacetonitrile in 300 ml of dry toluene was added dropwise to a suspension of 40.3 g (0.84 mole) of 50% sodium hydride (mineral oil was removed by washing with ligroin) in 800 ml of dry toluene at 80° C. The mixture was heated to 80°–85° C. for 1 hr. and the benzene solution of 1-benzyl-3-pyrrolidinemethanesulfonate (prepared above) was added dropwise while maintaining the temperature. The solution was stirred for 2 hr. at 85° C., cooled and extracted twice with water. The organic layer was dried over sodium sulfate and distilled. Yield 196 g (65%), b.p. 240°–250° C./0.5 mm.

A sample (15 g) was chromatographed on the HPLC (Water Prep LC/System 500 A) using Prep Pak 500 silica column and isopropyl ether. An impurity was first to emerge followed by the two diastereomers which were partially separated. That portion of the first emerging isomer which was shown by T.L.C. (silica gel; ethyl acetate) to be pure was collected and concentrated. Yield 4 g (27%) of racemic mixture.

Analysis: Calculated for $C_{24}H_{22}N_3Cl$: C, 74;31; H, 5.72; N, 10.83. Found: C, 74.38; H, 5.69; N, 10.96.

PREPARATION 19

α-(4-Chlorophenyl)-α-[1-(phenylmethyl)-3-pyrrolidinyl]-2-pyridineacetonitrile β isomer

*Diastereoisomer designated β-isomer as second emerging from the HPLC column.

To a solution of 136 g (0.77 mole) of 1-benzyl-3-pyrrolidinol and 78 g (0.79 mole) of triethylamine in 600 ml of dry benzene was added dropwise 8.86 g (0.77 mole) of methanesulfonyl chloride while cooling with an ice bath. The ice bath was removed and the mixture stirred 1 hr. and filtered. The filter cake was washed twice with 100 ml of benzene.

In a separate flask 175 g (0.77 mole) of α-(4-phenyl)-2-pyridylacetonitrile in 300 ml of dry toluene was added dropwise to a suspension of 40.3 g (0.84 mole) of 50% sodium hydride (mineral oil was removed by washing with ligroin) in 800 ml of dry toluene at 80° C. The mixture was heated to 80°–85° C. for 1 hr. and the benzene solution of 1-benzyl-3-pyrrolidinemethanesulfonate (prepared above) was added dropwise while maintaining the temperature. The solution was stirred for 2 hr. at 85° C., cooled and extracted twice with water. The organic layer was dried over sodium sulfate and distilled. Yield 196 g (65%), b.p. 240°–250° C./0.5 mm.

A sample (15 g) was chromatographed on the HPLC (Water Prep LC/System 500 A) using Prep Pak 500 silica column and isopropyl ether. An impurity was first to emerge followed by the two diastereomers which were partially separated. That portion of the second emerging isomer which was shown by T.L.C. (silica gel; ethyl acetate) to be pure was collected and concentrated. Yield 4.5 g (30%) of racemic mixture.

Analysis: Calculated for $C_{24}H_{22}N_3Cl$: C, 74.31; H, 5.72; N, 10.83. Found: C, 74.33; H, 5.71; N, 10.95.

PREPARATION 20a AND b

3-[α-(4-Chlorophenyl)-α-(2-pyridinyl)-cyanomethyl]-1-pyrrolidinecarboxylic acid, phenyl ester α isomer and β isomer Following the procedure of Preparation 5, the title compound is obtained by reacting α-(4-chlorophenyl)-α-[1-(phenylmethyl)-3-pyrrolidinyl]-2-pyridineacetonitrile α isomer (Preparation 18) with phenylchloroformate in pyridine-methylene chloride solvent.

The β-isomer is prepared from the corresponding starting material α-(4-chlorophenyl)-α-[(phenylmethyl)-3-pyrrolidinyl]-2-pyridineacetonitrile β-isomer (Preparation 19).

PREPARATION 21a AND b

α-(4-Chlorophenyl)-α-(2-pyridinyl)-3-pyrrolidineacetamide α isomer and β isomer

Following the procedure of Preparation 15, the title compound is prepared by subjecting 3-[α-(4-chlorophenyl)-α-(2-pyridinyl)-cyanomethyl]-1-pyrrolidinecarboxylic acid, phenyl ester α-isomer (Preparation 20a) to hydrolysis with hot 90% sulfuric acid.

The β-isomer is prepared from the corresponding starting material: 3-[α-(4-chlorophenyl)-α-(2-pyridinyl)-cyanomethyl]-1-pyrrolidinecarboxylic acid, phenyl ester β-isomer (Preparation 20b).

PREPARATION 22a AND b

Following the procedure of Preparation 2,
3-hydroxyhomopiperidine, and
4-hydroxyhomopiperidine
are reacted with p-toluenesulfonyl chloride to give the following:
(a) 1-[(4-methylphenyl)sulfonyl]-3-homopiperidinol-4-methylphenylsulfonate ester hydrochloride, and
(b) 1-[(4-methylphenyl)sulfonyl]-4-homopiperidinol-4-methylphenylsulfonate ester hydrochloride.

PREPARATION 23a AND b

Following the procedure of Preparation 12,
1-[(4-methylphenyl)sulfonyl]-3-homopiperidinol-4-methylphenylsulfonate ester, and
1-[(4-methylphenyl)sulfonyl]-4-homopiperidinol-4-methylphenylsulfonate ester
are reacted with sodium hydride and diphenylacetonitrile to give the following:
(a) α,α-diphenyl-1-[4-(methylphenyl)sulfonyl]-3-homopiperidinolacetonitrile, and
(b) α,α-diphenyl-1-[4-(methylphenyl)sulfonyl]-4-homopiperidinolacetonitrile.

PREPARATION 24a AND b

Following the procedure of Preparation 13,
α,α-diphenyl-1-[4-(methylphenyl)sulfonyl]-3-homopiperidinolacetonitrile, and
α,α-diphenyl-1-[4-(methylphenyl)sulfonyl]-4-homopiperidinolacetonitrile
are subjected to refluxing 48% hydrobromic acid in phenol to give the following:
(a) α,α-diphenyl-3-homopiperidineacetonitrile, and
(b) α,α-diphenyl-4-homopiperidineacetonitrile which may be isolated as hydrochloride salts as in Preparation 13.

PREPARATION 25a AND b

Following the procedure of Preparation 16,
α,α-diphenyl-3-homopiperidineacetonitrile and
α,α-diphenyl-4-homopiperidineacetonitrile
are hydrolyzed with conc. sulfuric acid (90%) to give the following:
(a) α,α-diphenyl-3-homopiperidineacetamide, and
(b) α,α-diphenyl-4-homopiperidineacetamide.

The following examples serve to illustrate the preparation of the novel compounds of Formula I, useful in treating cardiac arrhythmias in the method of this invention. The scope of the invention is not, however, limited thereto.

EXAMPLE 1

1-[[(Dimethylamino)methyl]carbonykl]-α,α-diphenyl-3-pyrrolidineacetamide hydrochloride hemihydrate To a stirred solution of 7.0 g (0.025 mole of α,α-diphenyl-3-pyrrolidineacetamide and 3.07 g of sodium carbonate in 150 ml of tetrahydrofuran was added 3.05 g (0.027 mole) of chloroacetylchloride. The solution was stirred 1.5 hr and 12 g (0.11 mole) of 40% aqueous dimethylamine was added. The solution was stirred an additional 3 hr and then concentrated. The residue was taken up in 100 ml of water and 50 ml of 10% aqueous sodium hydroxide and extracted with methylene chloride. The extracts were dried over magnesium sulfate and concentrated to yield 8.00 g (88%) residue as crude free base of the title compound. The hydrochloride salt was prepared in isopropyl alcohol with ethereal hydrogen chloride. Additional ether was added to totally precipitate the salt. Recrystallization from isopropyl alcohol-isopropyl acetate gave 3.0 g (29%) of the hydrochloride hemihydrate, softening point 183°-185° C., m.p. 192°-196° C.

Analysis: Calculated for $C_{22}H_{8c\ 29}ClN_3O_{2.5}$: C, 64.30; H, 7.11; N, 10.22. Found: C, 64.42; H, 7.05; N, 9.86.

EXAMPLE 2

Following the procedure of Example 1 but substituting the following for α,α-diphenyl-3-pyrrolidineacetamide:
α,α-diphenyl-3-piperidineacetamide, and
α,α-diphenyl-4-piperidineacetamide,
there are obtained:
1-[[(dimethylamino)methyl]carbonyl]-α,α-diphenyl-3-piperidineacetamide hydrochloride, and
1-[[(dimethylamino)methyl]carbonyl]-α,α-diphenyl-4-piperidineacetamide hydrochloride.

EXAMPLE 3

Following the procedure represented by the above equations for Method A and as in Example 1, but substituting the following for α,α-diphenyl-3-pyrrolidineacetamide:
α,α-diphenyl-3-pyrroldineacetonitrile,
α,α-diphenyl-3-piperidineacetonitrile, and
α,α-diphenyl-4-piperidinacetonitrile
there are obtained:
1-[[(dimethylamino)methyl]carbonyl]-α,α-diphenyl-3-pyrrolidineacetonitrile hydrochloride,
1-[[(dimethylamino)methyl]carbonyl]-α,α-diphenyl-3-piperidineacetonitrile hydrochloride, and
1-[[(dimethylamino)methyl]carbonyl]-α,α-diphenyl-4-piperidineacetonitrile hydrochloride.

EXAMPLE 4

1-[[[2-(Dimethylamino)ethyl]amino]carbonyl]-α,α-diphenyl-3-pyrrolidineacetamide fumarate hydrate To a stirred solution of 3.89 g (0.024 mole) of 1,1'-carbonyldiimidazole in 100 ml of tetrahydrofuran was added 1.93 g (0.022 mole) of N,N-dimethylethylenediamine. The solution was stirred at ambient temperature for 1.5 hr and 5.60 g of α,α-diphenyl-3-pyrrolidineacetamide was added. The solution was refluxed for 3.5 hr, cooled and concentrated. The residue obtained was dissolved in methyl chloride, washed with water, dried over magnesium sulfate and concentrated to give 8.40 g of crude free base of the title compound as white powdered glass. The free base was dissolved in isopropyl alcohol and reacted with fumaric acid. The solution was heated and isopropyl acetate was added until the cloud point was reached. The solution was cooled and filtered to give the fumarate salt. The salt was air dried for 18 hr to give 3.50 g (33%) of a white powder, m.p., softens 85°–90° C.; melts 120°–130° C. with decomposition.

Analysis: Calculated for $C_{27}H_{36}N_4O_7$: C, 61.35; H, 6.86; N, 10.60. Found: C, 61.54; H, 6.67; N, 10.51.

EXAMPLE 5

1-[[[2-(Dimethylamino)ethyl]amino]carbonyl]-α,α-diphenyl-3-piperidineacetamide fumarate hemihydrate A solution of 4.37 g (0.027 mole of 1,1'-carbonyldiimidazole and 2.11 g (0.024 mole) of N,N-dimethylethylenediamine in 150 ml of dimethylformamide was stirred for 1.5 hr at ambient temperture. To the solution was added 6.40 g (0.021 mole) of α,α-diphenyl-3-piperidineacetmide and the resulting solution was refluxed for 18 hr, cooled and concentrated. The residue was taken up in 100 ml of methylene chloride and 50 ml of water. The layers were separated and the aqueous layer was extracted with 50 ml of methylene chloride. The combined extracts were dried over magnesium sulfate and concentrated to give 8.40 g of crude free base of the title compound. The free base was dissolved in isopropyl alcohol and reacted with fumaric acid. Diethyl ether was added to precipitate the fumarate salt. The salt was dissolved in methanol and diethyl ether was added until precipitation was complete. The salt was separated and air dried for 18 hr to give 4.50 g (40%) of a white powder, m.p. 202°–203° C.

Analysis: Calculated for $C_{28}H_{37}N_4O_{6.5}$: C, 63.02; H, 6.99; N, 10.50. Found: C, 63.25; H, 7.00; N, 10.39.

EXAMPLE 6

1-[[[(2-(Dimethylamino)ethyl]amino]carbonyl]-α,α-diphenyl-4-piperidineacetamide fumarate sesquihydrate To a stirred solution of 2.75 g (0.017 mole) of 1,1'-carbonyldiimidazole in 100 ml of tetrahydrofuran was added 1.32 g (0.015 mole) of N,N-dimethylethylenediamine. The solution was stirred for 1.5 hr and 4.00 g (0.013 mole) of α,α-diphenyl-4-piperidineacetamide in 50 ml of tetrahydrofuran was added. The solution was refluxed for 18 hr, cooled and concentrated. The residue was taken up in methylene chloride, and the solution was washed with three 50 ml portions of water and extracted with two 200 ml portions of 1N sulfuric acid. The acidic extracts were made basic and extracted with methylene chloride. The methylene chloride extracts were dried over magnesium sulfate and concentrated to give 3.40 g of the free base of the title compound as a white glassy solid. The free base was recrystallized from ethyl acetate/ethyl alcohol to give 1.90 g (35%) crystals. The crystalline solid was dissolved in methanol and reacted with fumaric acid. The fumarate salt was precipitated by addition of diethyl ether to give 1.60 g (22%) crystals, m.p. softens 80° C., melts 133°–135° C.

Analysis: Calculated for $C_{28}H_{39}N_4O_{7.5}$: C, 60.96; H, 7.13; N, 10.16. Found: C, 60.60; H, 6.78; N, 10.29.

EXAMPLE 7

1-[[[2-(Dimethylamino)ethyl]amino]carbonyl]-α,α-diphenyl-3-homopiperidinoacetamide Following the procedure of Example 5, and substituting α,α-diphenyl-3-homopiperidineacetamide for α,α-diphenyl-3-piperidineacetamide, the title compound is prepared.

EXAMPLE 8

1-[[[2-(Dimethylamino)ethyl]amino]carbonyl]-α,α-diphenyl-4-homopiperidinoacetamide Following the procedure of Example 6, and substituting α,α-diphenyl-4-homopiperidineacetamide for α,α-diphenyl-4-piperidine, the title compound is prepared.

EXAMPLE 9

1-[[[2-(Dimethylamino)ethyl]amino]carbonyl]-α,α-diphenyl-3-homopiperidineacetonitrile Following the procedure of Example 5, and substituting α,α-diphenyl-3-homopiperidineacetonitrile for α,α-diphenyl-3-piperidineacetamide, the title compound is prepared.

EXAMPLE 10

1-[[[2-(Dimethylamino)ethyl]amino]carbonyl]-α,α-diphenyl-4-homopiperidineacetonitrile Following the procedure of Example 6 and substituting α,α-diphenyl-4-homopiperidineacetonitrile for α,α-diphenyl-4-piperidineacetamide, the title compound is prepared.

EXAMPLE 11

1-[[(Dimethylamino)methyl]carbonyl]-α,α-diphenyl-3-homopiperidineacetamide

Following the procedure of Example 1 and substituting α,α-diphenyl-3-homopiperidineacetamide for α,α-diphenyl-3-pyrrolidineacetamide, the title compound is prepared.

EXAMPLE 12

1-[[(Dimethylamino)methyl]carbonyl]-α,α-diphenyl-4-homopiperidineacetamide

Following the procedure of Example 1 and substituting α,α-diphenyl-4-homopiperidineacetamide for α,α-diphenyl-3-pyrrolidineacetamide, the title compound is prepared.

EXAMPLE 13a AND b

1-[[[2-(Dimethylamino)ethyl]amino]carbonyl]-α-(4-chlorophenyl), α-(2-pyridinyl)-3-pyrrolidinylacetamide α isomer and β isomer Following the procedure of Example 4, and α and β isomers of α-(4-chlorophenyl), α-(2-pyridinyl)-3-pyrrolidine acetamide as prepared by Preparations 21(a) and (b) are separately reacted with the reaction product of
(a) 1,1'-carbonyldiimidazole, and
(b) N,N-dimethylethylenediamine
to give the title products.

EXAMPLE 14a AND b

1-[[(Dimethylamino)methyl]carbonyl]-α-(4-chlorophenyl), α-(2-pyridinyl)-3-pyrrolidineacetamide α isomer and β isomer Following the procedure of Example 1, the α and β isomers of 2-(4-chlorophenyl), α-(2-pyridinyl)-3-pyrrolidine acetamide as prepared by Preparations 21(a) and (b) are separately reacted in sequence with
(a) chloroacetylchloride, and
(b) dimethylamine to give the title compounds.

EXAMPLE 15

1-[[[2-(Dimethylamino)ethyl]amino]thiocarbonyl]-α,α-diphenyl-4-piperidineacetamide fumarate Following the procedure of Example 6, and substituting 1,1'-thiocarbonyldiimidazole for 1,1'-carbonyldiimidazole, the title compound is prepared.

EXAMPLE 16

Following the procedure of Example 6, and substituting the following for N,N-dimethylethylenediamine:
N,N,N'-trimethylethylenediamine,
N,N-dimethyl-N'-phenylmethylethylenediamine,
N,N-dimethyl-N'-phenylethylenediamine,
N,N-dimethyl-N'-cyclohexylethylenediamine,
1-(2-aminoethyl)-pyrrolidine,
1-(2-aminoethyl)-piperidine,
1-(2-aminoethyl)-4-phenylpiperidine,
1-(2-aminoethyl)-2,6-dimethylpiperidine,
1-(2-aminoethyl)-4-hydroxy-4-phenylpiperidine,
1-(2-aminoethyl)-4-phenyl-1,2,3,6-tetrahydropyridine,
1-(2-aminoethyl)-4-tertiarybutoxycarbonylpiperazine,
1-(2-aminoethyl)-4-methylpiperazine,
1-(2-aminoethyl)-4-phenylpiperazine,
1-(2-aminoethyl)-4-(phenylmethyl)-piperazine, and 4-(2-aminoethyl)-morpholine
there are obtained:

(a) 1-[[[2-(dimethylamio)-1-methylethyl]amino]carbonyl]-α,α-diphenyl-4-piperidineacetamide,
(b) 1-[[[2-(dimethylamino)-1-(phenylmethyl)ethyl]amino]carbonyl]-α,α-diphenyl-4-piperidineacetamide,
(c) 1-[[[2-(dimethylamino)-1-phenylethyl]amino]carbonyl]-α,α-diphenyl-4-piperidineacetamide,
(d) 1-[[[2-(dimethylamino)-1-cyclohexylethyl]amino]carbonyl]-α,α-diphenyl-4-piperidineacetamide,
(e) 1-[[[2-(pyrrolidin-1-yl)ethyl]amino]carbonyl]-α,α-diphenyl-4-piperidineacetamide,
(f) 1-[[[2-(piperidin-1-yl)ethyl]amino]carbonyl]-α,α-diphenyl-4-piperidineacetamide,
(g) 1-[[[2-(4-phenylpiperidin-1-yl)ethyl]amino]carbonyl]-α,α-diphenyl-4-piperidineacetamide,
(h) 1-[[[2-(2,6-dimethylpiperidin-1-yl)ethyl]amino]carbonyl]-α,α-diphenyl-4-piperidineacetamide,
(i) 1-[[[2-(4-hydroxy-4-phenyl-piperidin-1-yl)ethyl]amino]carbonyl]-α,α-diphenyl-4-piperidineacetamide.
(j) 1-[[[2-(4-phenyl-1,2,3,6-tetrahydropyridin-1-yl)ethyl]amino]carbonyl]-α,α-diphenyl-4-piperidineacetamide,
(k) 1-[[[2-(4-t-butoxycarbonyl-piperazin-1-yl)ethyl]amino]carbonyl]-α,α-diphenyl-4-piperidineacetamide,
(l) 1-[[[2-(4-methyl-piperazin-1-yl)ethyl]amino]carbonyl]-α,α-diphenyl-4-piperidineacetamide,
(m) 1-[[[2-(4-phenyl-piperazin-1-yl)ethyl]amio]carbonyl]-α,α-diphenyl-4-piperidineacetamide,
(n) 1-[[[2-(4-phenylmethyl-piperazin-1-yl)ethyl]amino]carbonyl]-α,α-diphenyl-4-piperidineacetamide, and
(o) 1-[[[2-(4-morpholinyl)ethyl]amino]carbonyl]-α,α-diphenyl-4-piperidineacetamide.

PHARMACOLOGY

The action of compounds of this invention in correcting cardiac arrhythmias or preventing cardiac arrhythmias is demonstrated by the following procedures:

OUABAIN INDUCED ARRHYTHMIAS

Correcting of existing cardiac arrhythmias of ventricular origin is carried out on (1) adult mongrel dogs which are under barbiturate anesthesia during the test. A Grass Model 7 Polygraph was used for recording femoral arterial blood pressure (Statham P23AC Transducer) and the electrocardiogram (Grass 7P4 Preamplifier). Ouabian was given intravenously in an initial dose of 40 μg/kg and in a second dose of 20 μg/kg 30 minutes after the first dose and in subsequent doses of 10 μg/kg which were repeated at 15 min intervals as required for producing cardiac arrhythmias that persisted for at least 15 minutes. When the arrhythmias were established, the test compounds were administered by infusion (Harvard Model 942 Infusion Pump) into a femoral vein at a rate of 1 mg/kg/min. Concentration of compound was adjusted according to the weight of the dog to allow a volume infusion of 1 ml/min. The compound was considered to be active as antiarrhythmic agent if reversion to sinus rhythm occurred which was maintained for at least 30 min.

CORONARY ARTERY LIGATION INDUCED ARRHYTHMIAS

Adult mongrel dogs which are in the conscious state were used for the test and cardiac arrhythmias were induced by prior (22–24 hr) surgical preparation in which blood flow through a coronary artery was occluded by use of a constrictor device as reported by Smith et al, 1973. A Grass Model 79 Polygraph was used for recording the electrocardiogram (Grass 7P4 Preamplifier).

The test compound was administered by infusion (Harvard Model 942 Infusion Pump) into a saphenous vein to one group of dogs at a rate of 0.5 mg/kg/min. Concentration of compound was adjusted according to the weight of the dog to allow a volume of infusion of 0.5 ml/min. The test compound was administered orally by gavage to another group of dogs at dose levels of 10 through 40 mg/kg. The test compound was prepared in distilled water to give a total volume of 20 ml. Following the administration of the test compound, the heart rate, number of ectopic cardiac beats per min, and the percent ectopic beats (ectopic beats/HR X100) were recorded at 15 min. intervals. The compound was considered active if it abolished the ectopic ventricular frequency and caused a return to normal sinus rhythm within 2 hours of administration.

Data obtained demonstrating the antiarrhythmic activity of compounds of Formula I are in Table.

TABLE 1

Effect of Compounds on Cardiac Arrhythmias in Dogs

| | Arrhythmia Model | |
|---|---|---|
| Compound Example No. | Ouabain Induced[1] Correcting Dose, mg/kg, i.v. | Coronary Artery Ligation Induced[2] Correcting Dose, mg/kg, i.v. |
| 1 | — | 17 |
| 4 | 8–9 | 10–14 |
| 5 | 6.0 | 13 |

[1]Cardiac arrhythmias produced by method of Lucchessi and Hardman, 1961, J. Pharmacol. Exp. Therap. 132, 372–381.
[2]Cardiac arrhythmias produced by modification of method of Harris, 1950, Circulation 1, 1318, as reported by Smith et al, 1973, Pharmacologist 15, 192.
[3]Calculated as free base.

PHARMACEUTICAL COMPOSITIONS AND ADMINISTRATION

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal, parenteral or intracardial administration. Thus, for example, compositions for oral administration are preferably solids and can take the form of capsules, tablets or coated tables containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid; e.g., water, or a parenterally acceptable oil; e.g., arachis oil contained in ampoules.

In compositions for rectal administration the carrier can comprise a suppository base; e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on animals suggests the oral dosage effective to correct arrhythmias will be about 3 times that of the intravenous dosage. The animal data also suggest dosage requirements will be about half that of quinidine for the more active compounds.

Based on the animal data, allowing for variation in species and severity of cardiac arrhythmias, unit dosages containing an amount of compound equivalent to about 1 to about 100 mg/kg of body weight are contemplated. Based on all of the above considerations, a choice in a range of unit oral dosages for humans of about 10 to about 1000 mg is contemplated, preferably about 10 to 600 mg for a more active compound such as Example 4. Daily dosages of about 30 to 2400 mg are contemplated for humans and obviously several unit dosage forms may be administered at about the same time. However, the scope of the invention is not to be limited by these contemplations due to the uncertainty in transpositions discussed above.

Examples of unit dosage compositions are as follows:

| Capsules | |
|---|---|
| Ingredients | Per Cap. |
| 1. Active ingredient | 10.0 mg. |
| 2. Lactose | 146.0 mg. |
| 3. Magnesium Stearate | 4.0 mg. |

Procedure

1. Blend 1, 2 and 3.
2. Mill this blend and blend again.
3. This milled blend is then filled into #1 hard gelatin capsules.

| Tablets (10 mg) | |
|---|---|
| Ingredients | Mg./Tab. |
| 1. Active ingredient | 10.0 mg. |
| 2. Corn starch | 20.0 mg. |
| 3. Kelacid | 20.0 mg. |
| 4. Keltose | 20.0 mg. |
| 5. Magnesium Stearate | 1.3 mg. |

| Tablets (50 mg) | |
|---|---|
| Ingredients | Mg/Tab. |
| 1. Active ingredient | 50.0 mg. |
| 2. Milo starch | 20.0 mg. |
| 3. Corn starch | 38.0 mg. |
| 4. Lactose | 90.0 mg. |
| 5. Calcium stearate | 2.0 mg. |
| | 200.0 mg. |

Procedure

1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable table press.

| Intravenous Injection | |
|---|---|
| Ingredients | Per ml. |
| 1. Active ingredient | 1.0 mg. |
| 2. pH 4.0 Buffer solution | q.s. to 1.0 ml. |

Procesure

1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
|---|---|
| Ingredients | Per ml. |
| 1. Active ingredients | 5.0 mg. |
| 2. Isotonic Buffer solution 4.0 | q.s. to 1.0 ml. |

Procedure

1. Dissolve the active ingredient in the buffer solution.
2. Aseptically filter the solution from step #1.
3. The sterile solution is now aseptically filled into sterile ampuls.

4. The ampuls are sealed under aseptic conditions.

| Suppositories | |
|---|---|
| Ingredients | Per Supp. |
| 1. Active ingredient | 10.0 mg. |
| 2. Polyethylene Glycol 1000 | 1350.0 mg. |
| 3. Polyethylene Glycol 4000 | 450.0 mg. |

Procedure

1. Melt 2 and 3 together and stir until uniform.
2. Dissolve #1 in the molten mass from step 1 and stir until uniform.
3. Pour the molten mass from step 2 into suppository molds and chill.
4. Remove the suppositories from molds and wrap.

Therapeutic compositions having cardiac arrhythmia inhibiting activity in dosage unit form, comprising a pharmaceutical carrier and a cardiac arrhythmia inhibiting amount of a compound of Formula I or a pharmaceutically acceptable acid addition salt thereof are therefore an embodiment of this invention.

Various modifications and equivalents will be apparent to one skilled in the art and may be made in the compounds, method, and compositions of the present invention without departing from the spirit or scope thereof, and it is therefore to be understood that the invention is to be limited only by the scope of the appended claims.

What is claimed is:

1. A compound selected from the group having the formula:

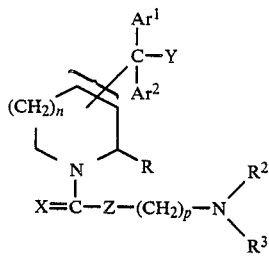

wherein;

n is selected from zero, one or two;
X is selected from oxygen or sulfur;
Z is selected from

or —CH$_2$—;

p is selected from 0 to 5 inclusive with the proviso that when Z is

p is at least one;
Y is selected from aminocarbonyl or cyano;
Ar$^1$ and Ar$^2$, which may be the same or different, are selected from the group consisting of phenyl or phenyl substituted by 1 to 3 radicals which may be the same or different selected from loweralkyl, loweralkoxy, halogen or trifluoromethyl;
R is selected from hydrogen or loweralkyl;
R$^1$ is, selected from the group consisting of hydrogen, cycloalkyl, loweralkyl, phenyl, phenyl substituted by halogen, loweralkyl, or loweralkoxy and phenyl-loweralkyl wherein phenyl may be substituted by halogen, loweralkyl or loweralkoxy and R$^2$ and R$^3$ are taken together with the adjacent nitrogen atom to form a heterocyclic residue selected from pyrrolidino, piperidino, 4-phenyl-piperidino, 2,6-diloweralkyl-piperidino, 4-hydroxy-4-phenyl-piperidino, 4-cyano-4-phenylpiperidino, piperazino, 4-loweralkylpiperazino, 4-phenylpiperazino, (4-phenylloweralkyl)-piperazino, or 4-morpholino radicals;
and when the side group

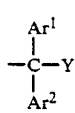

is in the 3-position and Ar$^1$ and Ar$^2$ are dissimilar, the diastereoisomers thereof; and the pharmaceutically acceptable acid addition salts thereof.

2. A compound selected from the group having the formula:

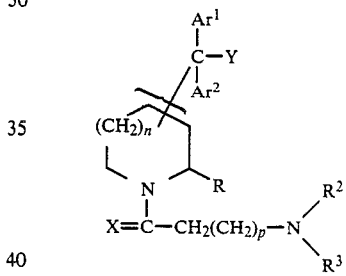

wherein;

n is selected from zero, one or two;
X is selected from oxygen or sulfur;
p is selected from 0 to 5 inclusive;
Y is selected from aminocarbonyl or cyano;
Ar$^1$ and Ar$^2$, which may be the same or different, are selected from the group consisting of phenyl or phenyl substituted by 1 to 3 radicals which may be the same or different selected from loweralkyl, loweralkoxy, halogen or trifluoromethyl;
R is selected from hydrogen or loweralkyl;
R$^2$ and R$^3$ are taken together with the adjacent nitrogen atom to form a heterocyclic residue selected from pyrrolidino, piperidino, 4-phenylpiperidino, 2,6-diloweralkyl-piperidino, 4-hydroxy-4-phenyl-piperidino, 4-cyano-4-phenylpiperidino, piperazino, 4-loweralkylpiperazino, 4-phenylpiperazino, (4-phenylloweralkyl)-piperazino, or 4-morpholino radicals;
and when the side group

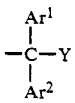

is in the 3-position and Ar¹ and Ar² are dissimilar, the diastereoisomers thereof; and the pharmaceutically acceptable acid addition salts thereof.

3. A compound selected from the group having the formula:

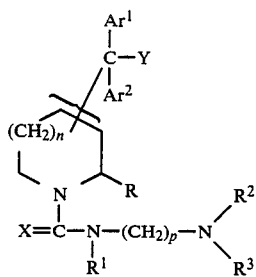

wherein;
n is selected from zero, one or two;
X is selected from oxygen or sulfur;
p is selected from 1 to 5 inclusive;
Y is selected from aminocarbonyl or cyano;
Ar¹ and Ar², which may be the same or different, are selected from the group consisting of phenyl or phenyl substituted by 1 to 3 radicals which may be the same or different selected from loweralkyl, loweralkoxy, halogen or trifluoromethyl;
R is selected from hydrogen or loweralkyl;
R¹ is, selected from the group consisting of hydrogen, cycloalkyl, loweralkyl, phenyl, phenyl substituted by halogen, loweralkyl, or loweralkoxy and phenyl-loweralkyl wherein phenyl may be substituted by halogen, loweralkyl or loweralkoxy and R² and R³ are taken together with the adjacent nitrogen atom to form a heterocyclic residue selected from pyrrolidino, piperidino, 4-phenyl-piperidino, 2,6-diloweralkyl-piperidino, 4-hydroxy-4-phenylpiperidino, 4-cyano-4-phenylpiperidino, piperazino, 4-loweralkylpiperazino, 4-phenylpiperazino, (4-phenylloweralkyl)-piperazino or 4-morpholino radicals;
and when the side group

is in the 3-position and Ar¹ and Ar² are dissimilar, the diastereoisomers thereof; and the pharmaceutically acceptable acid addition salts thereof.

4. A therapeutic composition for the treatment of cardiac arrhythmias comprising (a) an effective amount of a compound selected from the group having the formula:

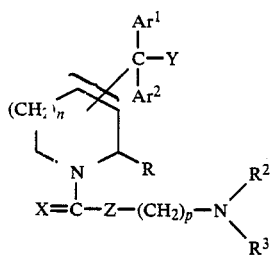

wherein;
n is selected from zero, one or two;
X is selected from oxygen or sulfur;
Z is selected from

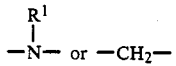

p is selected from 0 to 5 inclusive with the proviso that when Z is

p is at least one;
Y is selected from aminocarbonyl or cyano;
Ar¹ and Ar², which may be the same or different, are selected from the group consisting of phenyl or phenyl substituted by 1 to 3 radicals which may be the same or different selected from loweralkyl, lower alkoxy, halogen or trifluoromethyl;
R is selected from hydrogen or loweralkyl;
R¹ is, selected from the group consisting of hydrogen, cycloalkyl, loweralkyl, phenyl, phenyl substituted by halogen, loweralkyl, or loweralkoxy and phenyl-loweralkyl wherein phenyl may be substituted by halogen, loweralkyl or loweralkoxy and R² and R³ are taken together with the adjacent nitrogen atom to form a heterocyclic residue selected from pyrrolidino, piperidino, 4-phenylpiperidino, 2,6-diloweralkyl-piperidino, 4-hydroxy-4-phenylpiperidino, 4-cyano-4-phenylpiperidino, piperazino, 4-loweralkyl-piperazino, 4-phenylpiperazino, (4-phenylloweralkyl)-piperazino, or 4-morpholino radicals;
and when the side group

is in the 3-position and Ar¹ and Ar² are dissimilar, the diastereoisomers thereof; and the pharmaceutically acceptable acid addition salts thereof; and
(b) a pharmaceutically acceptable carrier thereofor.

5. A therapeutic composition for the treatment of cardiac arrhythmias comprising (a) an effective amount of a compound selected from the group having the formula:

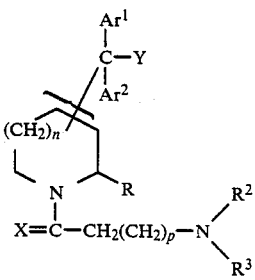

wherein;
n is selected from zero, one or two;
X is selected from oxygen or sulfur;
p is selected from 0 to 5 inclusive;

Y is selected from aminocarbonyl or cyano;

Ar¹ and Ar², which may be the same or different, are selected from the group consisting of phenyl or phenyl substituted by 1 to 3 radicals which may be the same or different selected from loweralkyl, loweralkoxy, halogen or trifluoromethyl;

R is selected from hydrogen or loweralkyl;

R² and R³ are taken together with the adjacent nitrogen atom to form a heterocyclic residue selected from pyrrolidino, piperidino, 4-phenylpiperidino, 2,6-diloweralkylpiperidino, 4-hydroxy-4-phenylpiperidino, 4-cyano-4-phenylpiperidino, piperazino, 4-loweralkylpiperazino, 4-phenylpiperazino, (4-phenylloweralkyl)-piperazino, or 4-morpholino radicals;

and when the side group $$\begin{array}{c} Ar^1 \\ | \\ -C-Y \\ | \\ Ar^2 \end{array}$$

is in the 3-position and Ar¹ and Ar² are dissimilar, the diastereoisomers thereof; the pharmaceutically acceptable acid addition salts thereof, and (b) a pharmaceutically acceptable carrier therefor.

6. A therapeutic composition for the treatment of cardiac arrhythmias comprising (a) an effective amount of a compound selected from the group having the formula:

wherein;

n is selected from zero, one or two;
X is selected from oxygen or sulfur;
p is selected from 1 to 5 inclusive;
Y is selected from aminocarbonyl or cyano;
Ar¹ and Ar², which may be the same or different, are selected from the group consisting of phenyl or phenyl substituted by 1 to 3 radicals which may be the same or different selected from loweralkyl, loweralkoxy, halogen or trifluoromethyl;

R is selected from hydrogen or loweralkyl;

R¹ is, selected from the group consisting of hydrogen, cycloalkyl, loweralkyl, phenyl, phenyl substituted by halogen, loweralkyl, or loweralkoxy and phenyl-loweralkyl wherein phenyl may be substituted by halogen, loweralkyl or loweralkoxy and R² and R³ are taken together with the adjacent nitrogen atom to form a heterocyclic residue selected from pyrrolidino, piperidino, 4-phenylpiperidino, 2,6-diloweralkyl-piperidino, 4-hydroxy-4-phenylpiperidine, 4-cyano-4-phenylpiperidino, piperazino, 4-loweralkyl-piperazino, 4-phenylpiperazino, (4-phenylloweralkyl)-piperazino, or 4-morpholino radicals;

and when the side group $$\begin{array}{c} Ar^1 \\ | \\ -C-Y \\ | \\ Ar^2 \end{array}$$

is in the 3-position and Ar¹ and Ar² are dissimilar; the diastereoisomers thereof; the pharmaceutically acceptable acid addition salts thereof; and (b) a pharmaceutically acceptable carrier therefor.

7. A method of treating cardiac arrhythmias in an animal which comprises administering to said animal an effective amount of a compound having the formula:

wherein;

n is selected from zero, one or two;
X is selected from oxygen or sulfur;
Z is selected from $$\begin{array}{c} R^1 \\ | \\ -N- \end{array}$$

or —CH₂;

p is selected from 0 to 5 inclusive with the proviso that when Z is $$\begin{array}{c} R^1 \\ | \\ -N-, \end{array}$$

p is at least one;

Y is selected from aminocarbonyl or cyano;

Ar¹ and Ar², which may be the same or different, are selected from the group consisting of phenyl or phenyl substituted by 1 to 3 radicals which may be the same or different selected from loweralkyl, loweralkoxy, halogen or trifluoromethyl;

R is selected from hydrogen or loweralkyl;

R¹ is, selected from the group consisting of hydrogen, cycloalkyl, loweralkyl, phenyl, phenyl substituted by halogen, loweralkyl, or loweralkoxy and phenyl-loweralkyl wherein phenyl may be substituted by halogen, loweralkyl or loweralkoxy and R² and R³ are taken together with the adjacent nitrogen atom to form a heterocyclic residue selected from pyrrolidino, piperidino, 4-phenylpiperidino, 2,6-diloweralkyl-piperidino, 4-hydroxy-4-phenylpiperidino, 4-cyano-4-phenylpiperidino, piperazino, 4-loweralkyl-piperazino, 4-phenylpiperazino, (4-phenylloweralkyl)-piperazino, or 4-morpholino radicals;

and when the side group $$\begin{array}{c} Ar^1 \\ | \\ -C-Y \\ | \\ Ar^2 \end{array}$$

is in the 3-position and $Ar^1$ and $Ar^2$ are dissimilar, the diastereoisomers thereof; and the pharmaceutically acceptable acid addition salts thereof.

8. A method of treating cardiac arrhythmias in an animal which comprises administering to said animal an effective amount of a compound having the formula:

wherein;

n is selected from zero, one or two;
X is selected from oxygen or sulfur;
p is selected from 0 to 5 inclusive;
Y is selected from aminocarbonyl or cyano;
$Ar^1$ and $Ar^2$, which may be the same or different, are selected from the group consisting of phenyl or phenyl substituted by 1 to 3 radicals which may be the same or different selected from loweralkyl, loweralkoxy, halogen or trifluoromethyl;
R is selected from hydrogen or loweralkyl;
$R^2$ and $R^3$ are taken together with the adjacent nitrogen atom to form a heterocyclic residue selected from pyrrolidino, piperidino, 4-phenylpiperidino, 2,6-diloweralkylpiperidino, 4-hydroxy-4-phenylpiperidino, 4-cyano-4-phenylpiperidino, piperazino, 4-loweralkylpiperazino, 4-phenylpiperazino, (4-phenylloweralkyl)-piperazino, or 4-morpholino radicals;

and when the side group $$\begin{array}{c} Ar^1 \\ | \\ -C-Y \\ | \\ Ar^2 \end{array}$$

is in the 3-position and $Ar^1$ and $Ar^2$ are dissimilar, the diastereoisomers thereof; and the pharmaceutically acceptable acid addition salts thereof.

9. A method of treating cardiac arrhythmias in an animal which comprises administering to said animal an effective amount of a compound having the formula:

wherein;

n is selected from zero, one or two;
X is selected from oxygen or sulfur;
p is selected from 1 to 5 inclusive;
Y is selected from aminocarbonyl or cyano;
$Ar^1$ and $Ar^2$, which may be the same or different, are selected from the group consisting of phenyl or phenyl substituted by 1 to 3 radicals which may be the same or different selected from loweralkyl, loweralkoxy, halogen or trifluoromethyl;
R is selected from hydrogen or loweralkyl;
$R^1$ is, selected from the group consisting of hydrogen, cycloalkyl, loweralkyl, phenyl, phenyl substituted by halogen, loweralkyl, or loweralkoxy and phenyl-loweralkyl wherein phenyl may be substituted by halogen, loweralkyl or loweralkoxy and $R^2$ and $R^3$ are taken together with the adjacent nitrogen atom to form a heterocyclic residue selected from pyrrolidino, piperidino, 4-phenylpiperidino, 2,6-diloweralkyl-piperidino, 4-hydroxy-4-phenylpiperidino, 4-cyano-4-phenylpiperidino, piperazino, 4-loweralkyl-piperazino, 4-phenylpiperazino, (4-phenylloweralkyl)-piperazino, or 4-morpholino radicals;

and when the side group $$\begin{array}{c} Ar^1 \\ | \\ -C-Y \\ | \\ Ar^2 \end{array}$$

is in the 3-position and $Ar^1$ and $Ar^2$ are dissimilar, the diastereoisomers thereof; and the pharmaceutically acceptable acid addition salts thereof.

* * * * *